(12) United States Patent
Pfeifer et al.

(10) Patent No.: US 10,512,714 B2
(45) Date of Patent: Dec. 24, 2019

(54) CATHETER

(71) Applicant: NovaPump GmbH, Jena (DE)

(72) Inventors: Joerg Pfeifer, Jena (DE); Patrick Patzer, Harth-Poellnitz (DE); Ronald Reich, Jena (DE)

(73) Assignee: NovaPump GmbH, Jena (DE)

( * ) Notice: Subject to any disclaimer, the term of this patent is extended or adjusted under 35 U.S.C. 154(b) by 18 days.

(21) Appl. No.: 15/449,744

(22) Filed: Mar. 3, 2017

(65) Prior Publication Data

US 2017/0173237 A1 Jun. 22, 2017

Related U.S. Application Data

(63) Continuation of application No. PCT/DE2015/100369, filed on Sep. 2, 2015.

(30) Foreign Application Priority Data

Sep. 3, 2014 (DE) .................. 10 2014 012 850

(51) Int. Cl.
*A61M 1/10* (2006.01)
*A61M 1/12* (2006.01)
(Continued)

(52) U.S. Cl.
CPC ........ *A61M 1/1008* (2014.02); *A61M 1/1074* (2014.02); *A61M 1/122* (2014.02); *A61M 1/125* (2014.02); *A61M 1/3666* (2013.01); *A61M 25/005* (2013.01); *A61M 25/0662* (2013.01); *A61M 25/09* (2013.01); *A61M 1/106* (2013.01);
(Continued)

(58) Field of Classification Search
CPC ...... A61M 1/008; A61M 1/122; A61M 1/125; A61M 1/3666
See application file for complete search history.

(56) References Cited

U.S. PATENT DOCUMENTS 5,460,607 A    10/1995  Miyata et al.
6,544,216 B1 *  4/2003  Sammler ........... A61M 25/0125
                                                    604/95.03
(Continued)

FOREIGN PATENT DOCUMENTS

DE        102014003153 A1    9/2015

OTHER PUBLICATIONS

International Search Report dated Mar. 11, 2016 of international application PCT/DE2015/100369 on which this application is based.

*Primary Examiner* — William J Levicky
(74) *Attorney, Agent, or Firm* — Walter Ottesen, P.A.

(57) ABSTRACT

The invention relates to a catheter for the directional conductance of a body fluid, particularly blood. The catheter includes a line segment which has a film tube defining an inner volume. A first port connects the inner volume to an external volume and a second port, arranged distally from the first port, connects the inner volume with the external volume. During operation of the catheter, the body fluid is conducted in the inner volume directionally between the first and second ports. The line segment includes a reinforcement running in the interior of the film tube. The film tube has a foldable section, a connecting region whereat the film tube is connected to the reinforcement, and a stabilized section having a structured profile.

14 Claims, 4 Drawing Sheets

(51) Int. Cl.
*A61M 1/36* (2006.01)
*A61M 25/00* (2006.01)
*A61M 25/06* (2006.01)
*A61M 25/09* (2006.01)

(52) U.S. Cl.
CPC ... *A61M 1/1072* (2013.01); *A61M 2025/0073* (2013.01); *A61M 2205/0266* (2013.01); *A61M 2205/04* (2013.01); *A61M 2210/125* (2013.01)

(56) References Cited

U.S. PATENT DOCUMENTS

| | | | |
|---|---|---|---|
| 7,070,555 B2 * | 7/2006 | Siess | A61M 1/1036 600/16 |
| 8,409,128 B2 | 4/2013 | Ferrari | |
| 8,932,246 B2 | 1/2015 | Ferrari | |
| 2003/0144573 A1 * | 7/2003 | Heilman | F04D 15/0022 600/16 |
| 2007/0197855 A1 | 8/2007 | Richardson et al. | |
| 2010/0268017 A1 * | 10/2010 | Siess | A61M 1/101 600/16 |
| 2014/0288354 A1 | 9/2014 | Timms et al. | |

* cited by examiner

CATHETER

CROSS REFERENCE TO RELATED APPLICATIONS

This application is a continuation application of international patent application PCT/DE2015/100369, filed Sep. 2, 2015, designating the United States and claiming priority from German application 10 2014 012 850.4, filed Sep. 3, 2014, and the entire content of both applications is incorporated herein by reference.

FIELD OF THE INVENTION

The present invention relates to a catheter for the directional conveyance of a body fluid, particularly blood, having a line segment with an internal volume, a first port which connects the internal volume to an external volume, and a second port, arranged distally from the first port, which connects the internal volume with the external volume, wherein during operation of the catheter the body fluid is conveyed in the internal volume directionally between the first and second ports.

"Distal" in the context of the invention means "toward the end of the catheter which has been inserted into the body". Accordingly, in the catheter according to the invention a second port arranged distally from a first port is arranged closer to the distal end of the catheter (that is, the catheter end which has been pushed into the body as intended) than the first port. "Proximal" in the context of the invention means "away from the distal catheter end". Accordingly, in the catheter according to the invention, a proximal end of the catheter is arranged opposite the distal catheter end, and typically protrudes out of the body when the catheter has been inserted into the body as intended.

BACKGROUND OF THE INVENTION

A catheter of the type mentioned is known in the prior art from, by way of example, U.S. Pat. Nos. 8,932,246 and 8,409,128. It is preferably used in cases of limited cardiac output to support the heart and the blood circulation. In particular, it can also be used in cases of higher-grade aortic insufficiency. It is used to transport the conveyed body fluid from a first location to another location, without increasing the pressure of the fluid at the first location significantly above the physiologically specified state, by utilizing the principle of a submersible pump, and preferably by the use of a balloon catheter combined with the principle of a diaphragm pump, wherein the term 'submerged pump' is used to mean a pump which is immersed in the fluid being conveyed, and the term 'diaphragm pump' is used to mean a pump with a drive which is separated by a membrane from the fluid being conveyed. Thus it allows, compared to the known method of intra-aortic balloon counterpulsation, a directional transport of the body fluid, as well as less stress on the patient.

Such catheters can be referred to as pump catheters as well. It is possible to use a separate drive in such a pump catheter. The catheter is then, in its basic form, merely a drive-less line catheter. The pump catheter can then be created, for example, by inserting an adjustable displacement device—for example, a balloon catheter of an intra-aortic balloon pump (IABP)—into the internal volume of the catheter after the line catheter has been placed. As such, it is reasonably possible to furnish the catheter without a drive as well.

The complexity, and the stress on the patient, of a minimally invasive insertion of a catheter into the body—for example via groin vessels—substantially depends on the size, particularly the largest outer diameter, of the catheter. Therefore, from the perspective of the patient and the attending physician, it is best for the outer diameter of the catheter to be as small as possible. On the other hand, in order to ensure the required pump power—that is, the volume of fluid to be transported per unit of time—along with the lowest possible loads on the fluid being transported, the largest possible inner diameter—at least in the section of the catheter through which the fluid must be transported—is advantageous.

SUMMARY OF THE INVENTION

In view of the foregoing, it is an object of the invention to provide a catheter of the type described above which has a high pumping capacity and a small outer diameter.

The catheter of the invention is for the directional conduction of a body fluid including blood. The catheter includes: a line segment including a film tube defining an inner volume; a first port connecting the inner volume to an external volume; a second port arranged distally from the first port and connecting the inner volume to the external volume; the film tube being configured to conduct the body fluid directionally in the inner volume thereof between the first and second ports during operation of the catheter; the line segment further including a reinforcement running in the inner volume of the film tube; and, the film tube having a foldable section, a connecting region wherein the film tube is connected to the reinforcement and a stabilizing section defining a structured profile.

According to the invention, the line segment comprises a film tube with a reinforcement running in the interior of the film tube, wherein the film tube has a foldable section, a connecting region in which the film tube is connected to the reinforcement, and a stabilized section with a structuring.

The property "foldable" means, in the context of the invention, that the film tube which is dimensionally stable up to a predetermined (relative) threshold low pressure relative to an external pressure, is not stabile at pressures lower than the threshold low pressure, wherein the instability arises at a relative pressure difference ΔP between the interior and the exterior of less than −500 mm Hg, and preferably less than −200 mm Hg.

As a result of the fact that the body fluid transporting section (line segment) of the catheter comprises a film tube, the catheter can have a greater internal diameter (preferably greater than 7 mm, and more preferably greater than 8 mm) in this section than in the prior art, such that the amount of fluid which can be transported through the catheter interior per time unit can be significantly higher than in the prior art. The foldable section makes a reversible folding state possible, which enables a minimally invasive insertion of the catheter into the body in spite of an inner diameter of the distal section which is larger than in the prior art. This is particularly advantageous in the field of cardiology since experience shows that a reduced implantation diameter of the cardiac catheter results in fewer patients of a particular patient population needing to be excluded from a procedure on account of their individual vessel inner diameter, and/or a higher fraction of patients can be directed to acute care without an additional vascular specialist needing to be present for support. In addition, the safety of the implantation and explanation can be improved by the smaller implantation diameter. For applications in cardiology, wherein the catheter is inserted, for example, in a minimally invasive manner into the heart via a groin vessel, the catheter can be advanced into the heart, and particularly in the region of a heart valve, in a manner which is significantly gentler to tissue than has been hitherto possible with conventional cardiac catheters, due to the foldable section.

The foldable section can comprise the line segment.

The foldable section is preferably folded when ready for use (that is, when able to be inserted into the body). This allows a further improvement in insertability into the patient's body. The folding can be random, or "ordered" in a predetermined pattern, and/or along predetermined fold lines. For example, the film material of the foldable section can be folded in a spiral or along one or more longitudinal folding lines. The folding can be maintained by a removable insertion sleeve which is pushed over the foldable section. This makes it possible to advance the catheter, when the foldable section is folded (compressed), via an access point at its determined point of entry in the body, and then to unfold the same by removing the insertion sleeve.

The connection of the film tube to the reinforcement and/or to an adjacent catheter section can be realized, for example, by welding (by way of example, cold welding or ultrasonic welding), or by gluing.

The stabilized section has an increased buckling resistance. In other words, the stabilized section has increased dimensional stability. In this way, once the catheter has been inserted into the body, it is possible to effectively prevent the film tube from buckling, for example at a place where the tube travels a tight loop due to anatomical/physiological conditions. Such a buckling is undesirable because the inner tube cross section which is reduced as a result of the buckling point can significantly reduce the amount of body fluid which can be transported through the film tube per unit of time. By way of example, if the catheter is inserted in the right heart for a procedure, the film tube can be arranged inside the right ventricle, with its distal end extending into the pulmonary artery. In this case, the film tube inscribes a tight loop in the right ventricle. It is possible to effectively prevent the tube from buckling at this point by means of a corresponding sectional stabilization of the film tube in the region of the loop.

As will be described below in more detail, the catheter can be advantageously configured for a pulsatile mode. The pressure fluctuations typically associated with pulsatile operation likewise do not lead to a (complete) buckling of the stabilized section. As such, the operational reliability of the catheter is significantly improved overall.

The foldable section can comprise the stabilized section.

The structuring of the stabilized section can preferably be a rib-shaped profiling. This enables effective stabilization in a simple manner. The buckling resistance can be adjusted by the configuration of the rib size, the rib spacing, et cetera. The ribs can be, by way of example, arranged transversely to the longitudinal direction of the film tube, or in a spiral. In an arrangement transverse to the longitudinal direction of the film tube, the ribs are each closed rings. In a spiral arrangement, one or more ribs are arranged in a coil form in the longitudinal direction of the film tube. Additionally or alternatively, it is possible that the film of the film tube is made thicker within the stabilized section, for example thicker by one-fifth or by one-half, than in an adjacent section.

Advantageously, the catheter can be configured in such a manner that the body fluid is suctioned through the first port into the internal volume (above and hereinafter also referred to as the catheter interior), conveyed in the internal volume in the distal direction, and discharged through the second port out of the internal volume. The configuration for transporting the body fluid in the distal direction of the catheter is particularly suitable for applications which support the pumping power of the right heart. The ports in this case are advantageously arranged in such a way, and the length of the film tube is configured in such a manner that, the catheter is inserted percutaneously into the human body and into the right heart via a central vein, the first port is positioned in the region of the right ventricle and the film tube extends from the right ventricle into the pulmonary artery, such that the second port is arranged in the pulmonary artery. As such, for the purpose of supporting the right ventricle, blood can be taken up in the right ventricle into the catheter, conveyed directionally in the internal volume to the region of the pulmonary artery, and discharged at that point out of the catheter. According to another advantageous embodiment, the right heart is bypassed by the line segment of the catheter. In this case, the first port lies in front of the right heart in the flow direction of the blood stream, for example in the inferior vena cava, the point where blood is taken up and transported through the entire right heart in the internal volume, then discharged out of the catheter through the second port in the pulmonary artery.

The film tube has a length of between 10 cm and 30 cm, preferably between 15 cm and 20 cm, and is ideally about 17 cm long; this is especially true in cases where the catheter is intended for use in the right heart.

The film tube has a wall thickness of particularly less than 0.6 mm, and preferably less than 0.3 mm.

The material of the film tube can comprise a plastic, preferably an elastomer such as a polyurethane, or a thermoplastic such as polyethylene. The material should be suitable for intracorporeal applications.

As previously explained in detail, the catheter according to the invention can thus have a film tube which is divided into sub-sections, wherein the sub-sections can, for example, each differ from each other in wall thickness (within the above range), material composition, material density, buckling resistance, pressure resistance, diameter and/or structuring of the inner and/or outer surface.

Preferably, the film tube is exactly or substantially radially symmetric or rotationally symmetric (infinite radial symmetry) about a longitudinal axis, at least in sections, particularly outside of its ends, and in particular is cylindrical, and the first port and/or the second port is/are arranged in a shell surface (surrounding the longitudinal axis), in particular a cylinder shell surface, of the film tube. The least outer diameter then corresponds to the cross section of the longitudinal axis. Higher-order radial symmetry advantageously leads to smaller least outer diameters.

The reinforcement is advantageously established by a guide tube, for example a commercially available angiographic catheter or the like, which has a further lumen (hereinafter also referred to as the tube interior). Preferably, the guide tube has an outer diameter between 0.5 mm and 2 mm.

Preferably, the guide tube is configured to be moved via a guidewire for the intended positioning of the catheter. Because the reinforcement additionally assumes the function of a guide tube which can be moved via a guidewire, the catheter can be implanted using the Seldinger technique known in cardiology, for example. In this case, the catheter preferably has a third proximal port, and the guide tube runs from this proximal port through the catheter to the second port. The distal end of the guide tube can pass through the second port. The tip of the guide tube is preferably curved back.

The distal end of the guide tube advantageously comprises a medication port. Alternatively or additionally, an (additional) medication port can also be arranged in the area of the second port. The medication port connects the tube interior (of the guide tube) to the outside, such that the inside of the tube communicates via this medication port with the exterior. In this way it is possible to administer a medication to the body via the guide tube when the catheter has been inserted into the body, the medication being discharged from the catheter through the medication port, by way of example locally in the area of the body which surrounds the medication port, and being able to achieve its effect in a faster and/or more targeted manner.

Advantageously, the film tube can have a plurality of second ports. The second ports can be at least partially arranged at a distance from the distal end of the film tube. By providing a plurality of second ports, their (total) port cross-section can be effectively increased, such that the body fluid transported distally can be released with lower local pressures from the catheter interior. The forces acting on the film tube, the body fluid, and the body tissue surrounding the second ports can thus be reduced advantageously.

The film tube preferably has a distal section which is particularly expanded bulbously, with an average outer diameter which is enlarged (relative to the adjacent section), and the second ports are arranged distributed within this section. Such an arrangement of the second ports results in the body fluid exiting the catheter in different directions, so that the forces acting on the film tube, the body fluid, and the body tissue surrounding the second ports, in particular in the case of a non-continuous, pulsatile—that is, surging and/or intermittent—transport of the body fluid can be further reduced, wherein it is particularly possible to prevent a "beating" of the distal end of the film tube due to the pressure fluctuations associated with the pulsatile transport (systole and diastole in the use of the catheter as a heart catheter).

The catheter preferably includes (in addition to the line segment) a pump chamber section. One or more connecting sections can be arranged between the line segment and the pumping chamber section. The envelope of the pump chamber section can be formed by the film tube. The pump chamber section can be wholly or partially a subsection of the line segment. The pump chamber section can be wholly or partially a subsection of the foldable section. Appropriately, the first port is arranged in the region of one end of the line segment, and the second port is arranged in the region of an opposite end of the line segment.

In a preferred embodiment, the first port is arranged in the region of the pump chamber section. In this case, the pump chamber section forms a part of the line segment, such that the pump chamber is a part of the line.

In a further suitable embodiment, however, the first port can be arranged outside of the pump chamber section in the line segment.

Typically, the catheter has a larger inner diameter in the region of the pump chamber section than in the region of the line segment adjoining the pump chamber section area. In particular, the pump chamber section has an average internal diameter greater than 15 mm.

The pump chamber section can include a pump chamber. The pump chamber preferably has a (deployable) frame. The material of the frame preferably comprises a composition comprising a shape memory alloy, in particular nitinol, a shape memory polymer, or a shape memory ceramic. The frame has a substantially tubular configuration. Preferably, the frame is exactly or substantially radially symmetric or rotationally symmetric (infinite radial symmetry) about a longitudinal axis, at least in sections, particularly outside of its ends, or at least its outer sleeve ends, and in particular is cylindrical. In particular, the frame can be a deployable stent. In other words, the pump chamber section or at least the pump chamber can be foldable. The foldable section can thus include the pump chamber section and/or the pump chamber. The frame is preferably arranged in the interior of the pump chamber.

The pump chamber is preferably between 150 mm and 300 mm long.

The catheter preferably has a third port in its proximal region, such that a drive, in particular a balloon of a balloon catheter, in particular of an intra-aortic balloon pump catheter (IABP), can be passed through the third port into the interior of the catheter up to a predetermined final position relative to the catheter. The predetermined target position preferably corresponds to the pump chamber—that is, the balloon is preferably intended to be arranged in the pump chamber.

The drive can expediently be passed through the third port in such a manner that the same is closed off in a fluid-tight manner (that is, particularly at least with respect to a maximum blood pressure). A catheter according to U.S. Pat. No. 5,460,607 A can be used as the drive in the form of a displacement device, by way of example. The drive arranged in the interior can be connected to an external power source via a line leading through the third port—in the case of a balloon catheter, for example, via an auxiliary fluid line to a pump console (pump) which can fill and deflate the balloon with an auxiliary fluid, preferably intermittently. A directional transport of the body fluid is made possible by the displacing effect of the filled balloon. By way of example, the drive can be adjustable with respect to the frequency of the filling processes of the balloon with auxiliary fluid and/or the volume of the auxiliary fluid per filling.

In a particularly advantageous embodiment variant, the catheter is constructed in such a manner that the catheter has a pump chamber in which the balloon of an IAB catheter is permanently disposed. By means of a line for an auxiliary fluid which passes through the third port of the catheter to the outside, the balloon can be connected to an external pump, particularly a so-called IABP pump console. As such, the catheter is ready to use, without the additional steps of a subsequent introduction of a separate displacement device into the fluid being conveyed, and the insertion of the balloon into the interior of the line catheter. The implantation time is thereby reduced.

Helium is preferably used as the auxiliary fluid for filling the balloon.

A non-return valve can be arranged at the first port and/or the second port (to allow only unidirectional flow between the internal volume and the external space surrounding the catheter). The non-return valve is preferably configured as a diaphragm valve according to DE 10 2014 003 153.5, the disclosure of which is hereby incorporated in its entirety into the present invention. A plurality of diaphragm valves is preferably arranged inside the pump chamber section (particularly more than 50 or even more than 100 diaphragm valves). In this case, the individual diaphragm valves are preferably arranged in rows which are equally distributed and which extend along the pump chamber section.

Additionally or alternatively, it is possible that the foldable section and/or a subsection of the foldable section provides a valve function. This is preferably implemented in combination with a pulsatile operation of the catheter, wherein the periodic changes in the pressure conditions in the catheter interior due to the intermittent transport of the body fluid lead to the periodic collapse and subsequent expansion of the foldable section/subsection. By way of example, body fluid in the interior of the catheter can be pumped in a pulsatile manner in the distal direction by means of an inflatable balloon disposed proximally to the foldable section, by the body fluid being displaced distally by the volume increase of the balloon during filling, and escaping from the catheter through the second port arranged distally from the foldable section. The foldable section/subsection is expanded in this case due to the currently prevailing overpressure in the catheter. Subsequently, the balloon is evacuated, thereby producing a negative pressure in the catheter interior, which leads to the collapsing of the foldable section/subsection. As a result of the greatly reduced inner tube cross section in the region of the folding section/subsection, the valve action arises which effectively prevents backflow of distally displaced body fluid in the proximal direction.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
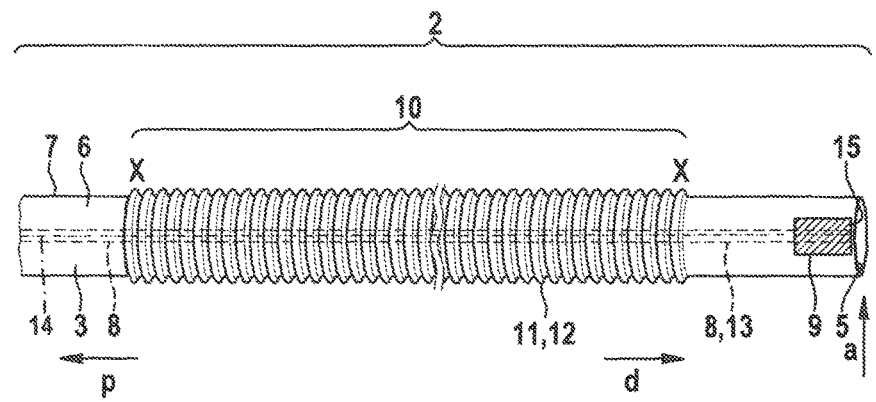
FIG. 1 shows a line segment of the catheter according to the invention, having a film tube which comprises a foldable section which has a stabilized section.

FIG. 1 shows the line segment 2 of a catheter 1 according to the invention. The direction arrows p and d illustrate the distal d and proximal p orientations. The line segment 2 comprises a film tube which surrounds an internal volume 3. The internal volume 3 communicates with the exterior X via a first port 4 (not shown) and a second port 5. The first port 4 is arranged at the proximal end of the line segment 2 and the second port 5 is arranged at the distal end of the line segment 2. A reinforcement 9 runs in the interior 3 of the film tube. For clarity, the reinforcement 8 is shown with dashed lines. The reinforcement 8 is connected to the film tube 6 near the distal end of the catheter 1 in a connecting region 9. In the embodiment of FIG. 1, the reinforcement 8 is configured as a guide tube 13. The guide tube 13 is adapted to be moved via a guidewire 14, and tot this purpose has at its distal end a tube port 15. As such, the catheter can be implanted into a patient's body in a simple manner using the Seldinger technique. The film tube has a foldable section 7. In the embodiment of FIG. 1, the foldable section 7 additionally comprises a stabilized section 10. The foldable section is characterized in that it can be packaged in an insertion sleeve (not shown) for better insertability of the catheter into the patient's body. The insertion sleeve has a physiologically favorable outer diameter of for example, less than 20 French. After puncturing and dilation of a groin vessel the catheter packaged in the insertion sleeve is advanced into the vessel. Then, the insertion sleeve is pulled back out of the vessel, thereby unpacking the foldable section 7. Because of its relative flexibility, the foldable section 7 can then be further advanced to its destination, for example the right ventricle 24, without damaging tissue.

Figure 2:
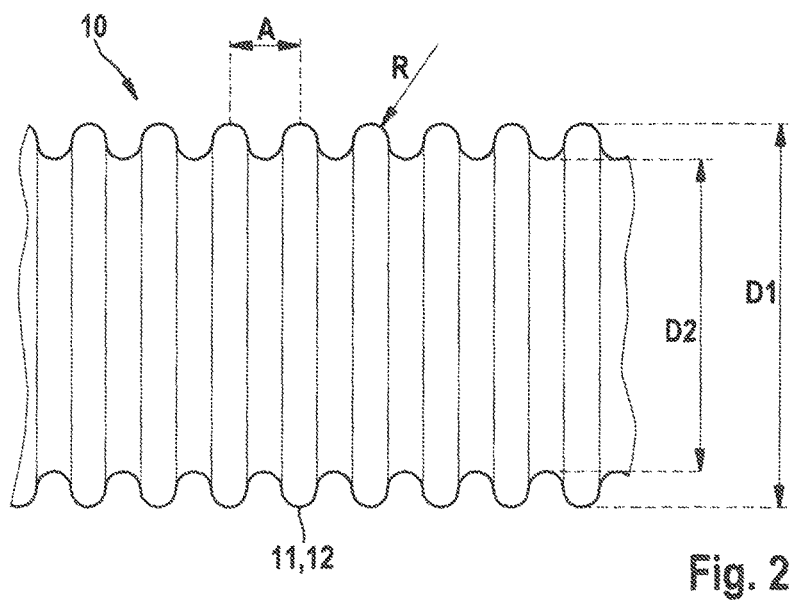
FIG. 2 shows a part of the stabilized section of the film tube according to FIG. 1.

The stabilized section 10 is structured in the form of ribs. This is easily seen in FIG. 2, which shows a section of the film tube of FIG. 1. The ribs are arranged periodically, transverse to the longitudinal direction, in the form of closed rings—that is, not helically. The nominal diameter of the stabilized section corresponds to the diameter at the crest of a rib D1; the core diameter of the stabilized section corresponds to the diameter of a rib base D2. In the embodiment of FIG. 2, the nominal diameter D1 is 9.6 mm, and the core diameter D2 is 8.1 mm. The distance between two ribs (ribs period A) in the present embodiment is 1.6 mm. The radius R of a rib is 0.45 mm.

Figure 3:
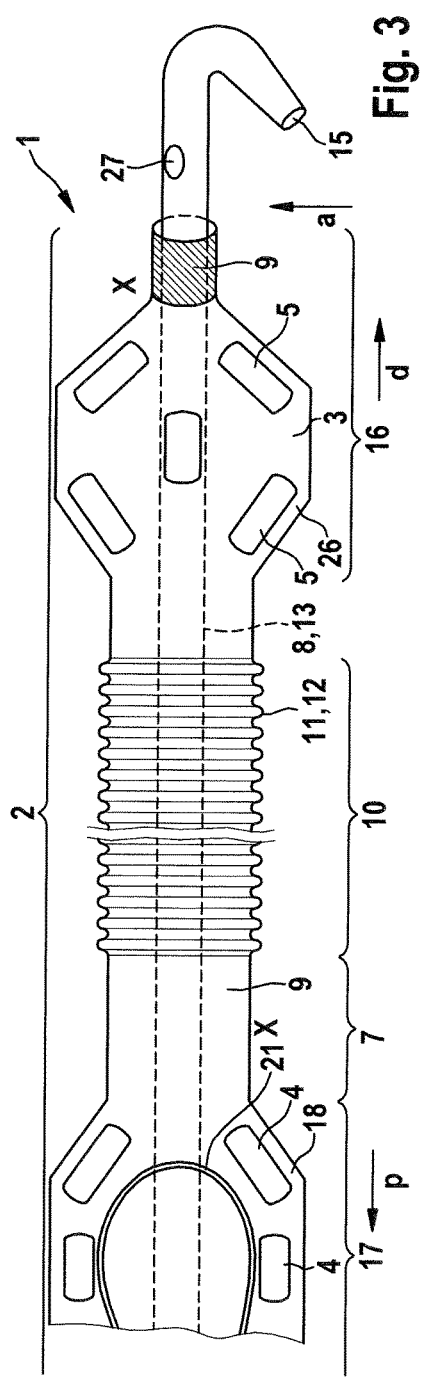
FIG. 3 shows an embodiment of the catheter with a bulbous enlarged distal section having a plurality of second ports.

FIG. 3 shows a further preferred embodiment of the catheter 1, wherein the catheter 1 further comprises a pump chamber section 17 arranged proximal to the film tube 6. The pump chamber section 17 include a pump chamber 16 and a balloon 21 of a balloon catheter, arranged inside the pump chamber 18. The balloon 21 is connected to a line 22 (FIG. 5) for an auxiliary fluid, which passes to the outside through a third proximal port 20 (FIG. 5) of the catheter (not shown to improve clarity). The balloon 21 can be connected to an external pump via this line, in particular to a so-called IBAP pump console. The balloon 21 can operate in a pulsatile manner—that is, can be filled and emptied with the auxiliary fluid intermittently—and thus serves as a drive for the directional transport of the body fluid. The catheter 1 according to FIG. 3 can thus be Advantageously used for intra-aortic balloon counterpulsation procedures. Furthermore, the catheter 1 has a bulbously enlarged distal section 16; 26 which includes a plurality of second ports 5. These are distributed inside the distal section 16; 26 in such a manner that the body fluid transported through the line segment 2 flows out of the second ports 5 in different directions. As a result, the forces acting on the film tube 6, the body fluid, and the body tissue surrounding the second ports 5, in particular in the case of a pulsatile transport of the body fluid, can be reduced, wherein it is particularly possible to prevent a "beating" of the film tube 6 due to the pressure fluctuations associated with the pulsatile transport (systole and diastole in the use the catheter 1 as a heart catheter).

Figure 4:
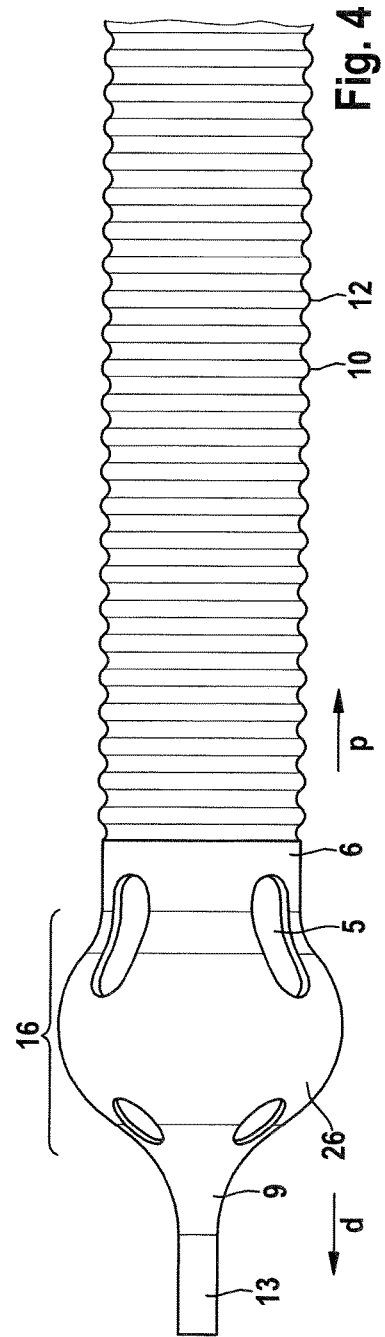
FIG. 4 shows a part of the film tube of a catheter according to the invention, having a distal bulbous enlarged section.

As can be seen in FIG. 4, the bulbously enlarged distal section 16; 26 can particularly preferably directly adjoin the connecting region 9 proximally. The transition from the connecting region 9 to the distal section 16; 26 can be configured, on the exterior thereof, in such a manner that there is a smooth transition which enables easy advancement of the catheter 1. In the interior of the catheter, the distal section forms a substantially spherical end piece.

Figure 5:
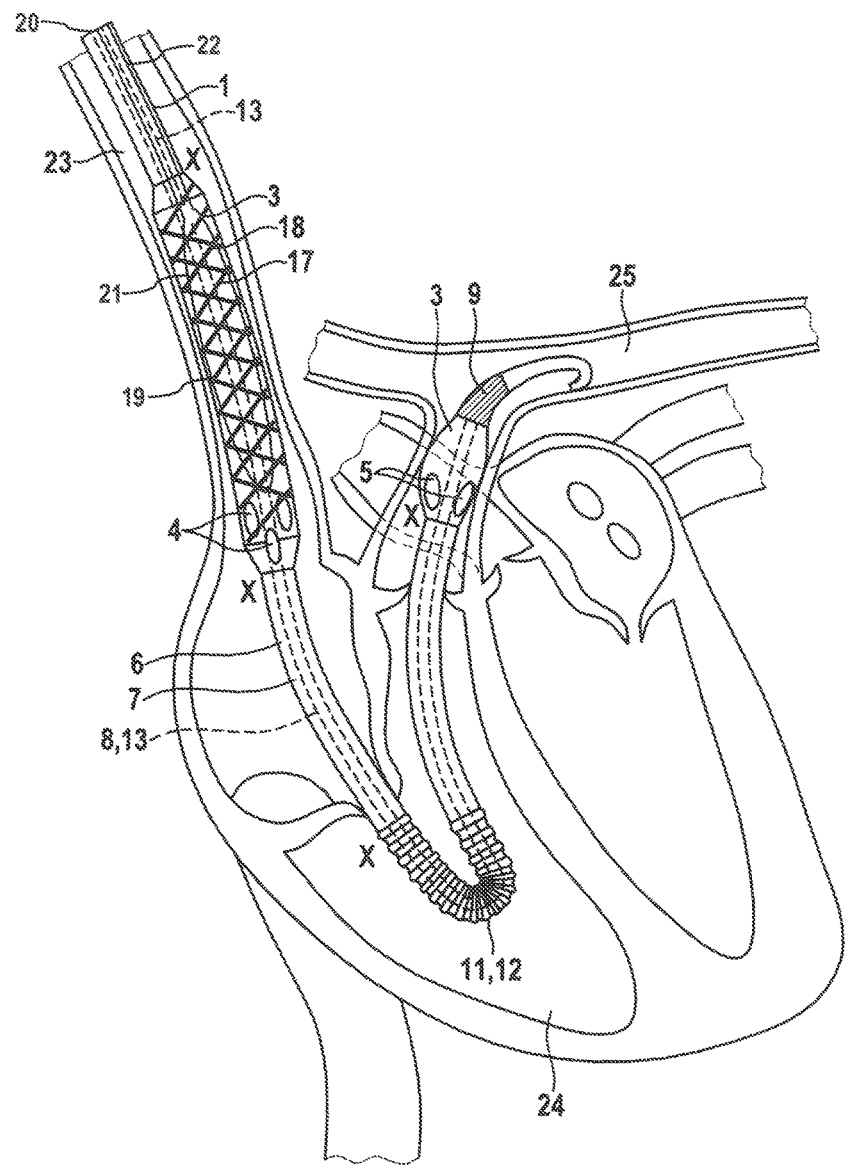
FIG. 5 shows the position of a catheter according to the invention in the right heart of a human patient (access via the superior vena cava), by way of example; and, FIG. 6 shows a further position example (access via the inferior vena cava) of a catheter according to the invention, in the right heart of a human patient.

FIG. 5 shows a typical application of the catheter 1 as a blood pump. For acute cardiac treatment, the catheter is implanted into a patient in a minimally invasive manner via a venous access in the neck. The access via the superior vena cava, as shown in FIG. 5, is purely exemplary in nature, and is only selected in this case for the sake of better illustration. In practice, however, cardiac catheters are often implanted via a groin access. The distal line segment 2 of the catheter is advanced into the right ventricle 24. The pump chamber section 17 with the pump chamber 18 is positioned in the superior vena cava 23. The pump chamber 18 is a part of the line segment 2. The pump chamber is adapted for a pulsatile mode—that is, a balloon 21 of a balloon catheter (not shown) is arranged inside the pump chamber. The balloon 21 is operated in a pulsatile manner in the embodiment of FIG. 4—that is, is filled and emptied intermittently with the auxiliary fluid—and thus serves as a drive for a directional flow of the blood. First ports 4 are arranged inside the pump chamber section 17. The blood is suctioned into the catheter 1 through the first ports 4, and is directionally transported distally to the second ports 5 in a pulsatile manner in the catheter interior 3 of the line segment 2, according to the drive frequency of the balloon (which can follow an ECG signal, for example), where it then exits the catheter. The distal end of the catheter 1 extends into the pulmonary artery 25. The line segment 2 of the catheter 1 therefore spans (bridges) the entire right heart. The second ports 5 lie, in the embodiment of FIG. 5, in the pulmonary trunk. The line segment 2—that is, both the pump chamber section 17 and the pump tube 6 adjoining the same distally—has a foldable configuration, and thus forms a foldable section 7. A deployable frame 19 is arranged inside the pump chamber 18, which provides sufficient rigidity for the pulsatile operation of the pump chamber 18. For the insertion of the catheter 1 into the body, the line segment 2 is packaged (not shown) in the folded state into an insertion sleeve. The accordingly packaged catheter is advanced via an access in the superior vena cava to the position of the line segment 2, which corresponds to the position shown in FIG. 5, and the line segment 2 penetrates the heart. The insertion sleeve is then withdrawn, whereby the frame 19 is deployed and the line segment 2 unfolds entirely. Due to the configuration of the line segment 2 as a foldable film tube 6, the sensitive heart valves are hardly damaged during the implantation and explanation. A buckling of the film tube 6 in anatomically critical areas within the heart is prevented by the stabilized section 10.

Figure 6:
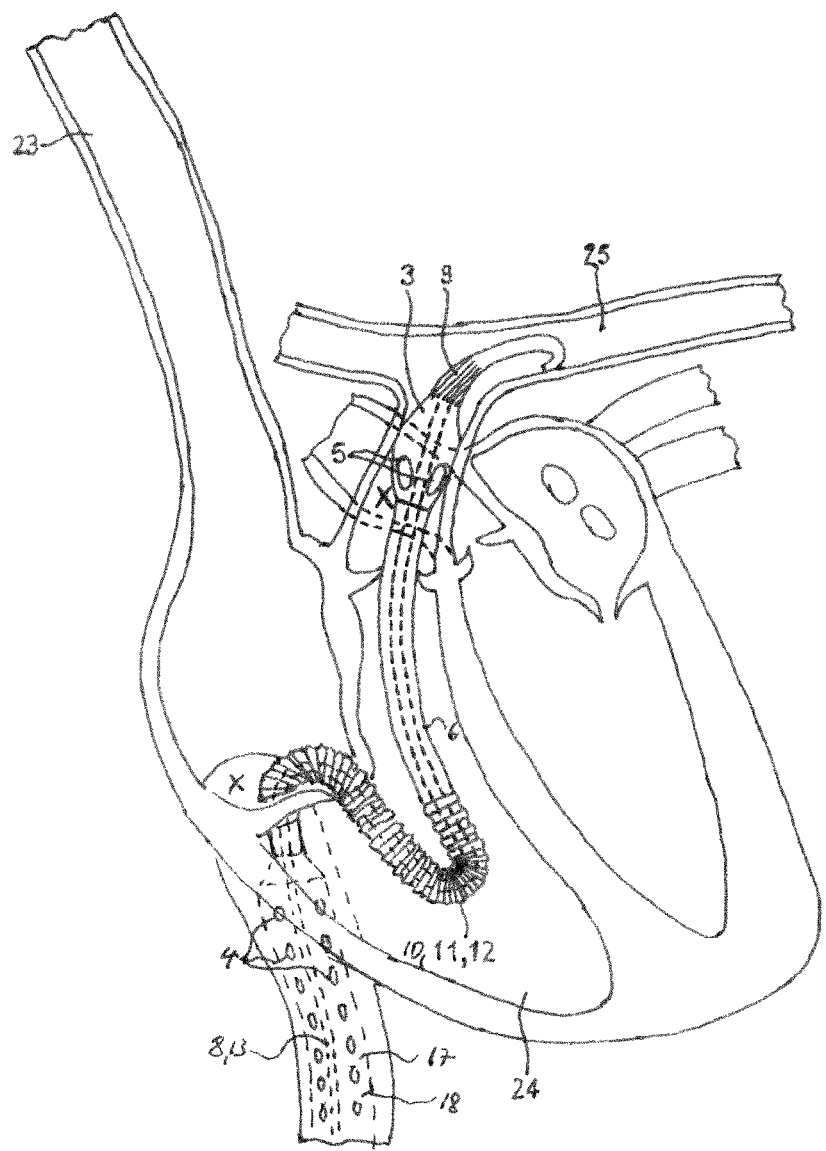

In FIG. 6, the catheter 1, which corresponds structurally to the catheter of FIG. 5, but can have different dimensions in its subsections, is routed via an alternative access of a groin vessel, and is advanced until the pump chamber section 17 is positioned with the first ports 4 in the functional position in the inferior vena cava. The pump tube 6 arranged distally from the pump chamber section spans the right atrium and the right ventricle and therefore extends with its distal end into the pulmonary artery 25. The second ports 5 are arranged in the region of the pulmonary trunk. As already mentioned, this variant routing is standard practice. The catheter, in particular, the length of the line segment 2, the length of the pump chamber section 17, the length of the distal pump tube and/or the position of the stabilized section 10 can be adjusted for optimal fit specifically to this variant routing. For example, the line segment 2 (including the pump chamber section 17) can have a length of 450 mm; the pump chamber section 17 is about 250 mm long, and the distally adjoining pump tube (film tube) 6 is about 200 mm long. The first ports 4 are configured as film valves which are arranged in five radially distributed rows of 20 valves each along the pump chamber section 17.

It is understood that the foregoing description is that of the preferred embodiments of the invention and that various changes and modifications may be made thereto without departing from the spirit and scope of the invention as defined in the appended claims.

LIST OF REFERENCE NUMBERS 1 catheter
2 line segment
3 internal volume
4 first port
5 second port
6 film tube
7 foldable section
8 reinforcement
9 connecting region
10 stabilized section
11 structuring
12 rib-shaped structuring
13 guide tube
14 guidewire
15 tube port
16 distal section
17 pump chamber section
18 pump chamber
19 frame
20 third port
21 balloon
22 auxiliary fluid line
23 superior vena cava
24 right ventricle
25 pulmonary artery
26 bulbous expanded section
27 medication port
d distal
p proximal
A rib period (spacing rib to rib)
D1 nominal diameter (rib peak)
D2 core diameter (rib base)
R rib radius
X external

What is claimed is:

1. A catheter for a directional conduction of a pulsating body fluid including blood, the catheter comprising:
   a line segment including a film tube defining an inner volume;
   a pump chamber section arranged proximally as an extension of said film tube;
   a first port connecting said inner volume town external volume;
   a second port arranged distally from the first port and connecting said inner volume to said external volume;
   said film tube being configured to conduct the pulsating body fluid directionally in said inner volume thereof between said first and second ports during operation of said catheter;
   said line segment further including a reinforcement running in said inner volume of said film tube;
   said film tube having a foldable section, a connecting region wherein said film tube is connected to said reinforcement and a stabilized section defining a structured profile as an integral part of said film tube disposed between said first and second ports;
   said pump chamber section defining a pump chamber and said pump chamber having a frame disposed therein;
   said frame having a composition which comprises a shape memory material;
   a third port communicating with said pump chamber;
   a balloon being arranged in said pump chamber and within said frame;

said frame made of said shape memory material providing sufficient rigidity for the pulsatile operation of said balloon disposed within said frame;

a line for an auxiliary fluid for inflating said balloon being connected to said balloon;

said line for the auxiliary fluid passing out through said third port of the catheter;

the outer end of the line being connectable to a pump for the auxiliary fluid; and, said balloon, when deflating, drawing body fluid into the catheter through the first port and, when inflating, driving the drawn-in body fluid in a distal direction through said film tube.

2. The catheter of claim 1, wherein said foldable section is folded in a ready to use state of said catheter.

3. The catheter of claim 1, wherein said structured profile is a rib-shaped profile.

4. The catheter of claim 1, wherein the catheter is configured so as to cause the body fluid to be drawn through said first port into said inner volume by suction, conducted in said inner volume in a distal direction and discharged through the second port out of said inner volume.

5. The catheter of claim 1, wherein the film tube has a wall thickness of less than 0.6 mm.

6. The catheter of claim 1, wherein the film tube has a wall thickness of less than 0.3 mm.

7. The catheter of claim 1, wherein a material of the film tube comprises a plastic.

8. The catheter of claim 1, wherein a material of the film tube comprises a polyurethane.

9. The catheter of claim 1, wherein the reinforcement includes a guide tube defining a guide tube interior; and, said guide tube has an outer diameter lying in a range between 0.5 mm and 2 mm.

10. The catheter of claim 9, wherein said guide tube is configured to be pushed over a guide wire for determinatively positioning the catheter.

11. The catheter of claim 10, wherein said guide tube has a distal end and a medication port at said distal end.

12. The catheter of claim 1, wherein the film tube has a distal end and comprises a plurality of second ports which are at least partially arranged at a distance from, said distal end of said film tube.

13. The catheter of claim 12, wherein said film tube has a distal section configured to be bulbously enlarged; and, said second ports are arranged distributed within said distal section.

14. The catheter of claim 1, wherein said shape memory material is one of the following: nitinol, a shape memory polymer, or a shape memory ceramic.

* * * * *

UNITED STATES PATENT AND TRADEMARK OFFICE
CERTIFICATE OF CORRECTION

PATENT NO. : 10,512,714 B2
APPLICATION NO. : 15/449744
DATED : December 24, 2019
INVENTOR(S) : Pfeifer et al.

Page 1 of 1

It is certified that error appears in the above-identified patent and that said Letters Patent is hereby corrected as shown below:

In the Specification

In Column 7:
Line 52: insert -- 6 -- after "a film tube".
Line 57: delete "A reinforcement 9" and substitute -- A reinforcement 8 -- therefor.
Line 63: delete "tot" and substitute -- for -- therefor.

In Column 8:
Line 28: delete "include" and substitute -- includes -- therefor.
Line 28: delete "pump chamber 16" and substitute -- pump chamber 18 -- therefor.
Line 34: delete "IBAP" and substitute -- IABP -- therefor.
Line 52: insert -- of -- after "in the use".

In the Claims

In Column 10:
Line 46: delete "town" and substitute -- to an -- therefor.

In Column 12:
Line 16: delete "," after "at a distance from".

Signed and Sealed this
First Day of December, 2020

Andrei Iancu
*Director of the United States Patent and Trademark Office*